United States Patent [19]
Parker

[11] 3,989,741
[45] Nov. 2, 1976

[54] PREPARATION OF ANTIOXIDANTS
[75] Inventor: Dane K. Parker, Canton, Ohio
[73] Assignee: The Goodyear Tire & Rubber Company, Akron, Ohio
[22] Filed: Jan. 22, 1974
[21] Appl. No.: 435,569

[52] U.S. Cl. .................... 260/486 R; 260/45.85 B; 260/410.5; 260/469; 260/471 R; 260/473 R; 260/473 F; 260/476 R; 260/488 CD; 260/592; 260/624 R; 260/625
[51] Int. Cl.² ........................................ C07C 69/54
[58] Field of Search............ 260/486 R, 410.5, 469, 260/471 R, 473 R, 473 F, 488 CD, 625, 592

[56] References Cited
OTHER PUBLICATIONS
March, J., Advanced Organic Chem: Reactions, Mechanisms & Structure, McGraw Hill Co., N.Y., 1968, pp. 357, 481, 678, & 322.

Primary Examiner—Paul J. Killos
Attorney, Agent, or Firm—F. W. Brunner; J. A. Rozmajzl

[57] ABSTRACT

This invention comprises an alkylation, reduction and transesterification process for the preparation of ester substituted phenols. The products are useful as antioxidants and may be prepared in high yields and with a high degree of purity.

8 Claims, No Drawings

PREPARATION OF ANTIOXIDANTS

The present invention relates to the preparation of ester substituted phenols that have a stabilizing effect on oxidizable organic materials when such materials are exposed to oxidative degradative conditions. More particularly, the invention relates to the preparation of these materials by a process involving steps of alkylation, reduction and transesterification to the materials produced by the process, and to organic materials stabilized with these materials.

Esters of the type of the present application are currently prepared by reacting materials such as methacryloyl chloride and alcohols as starting materials. Reactions using these acid chlorides are corrosive and require the use of special equipment such as glass lined reactors.

It is an object of the present invention to provide a process for manufacturing ester substituted phenols. It is a further object of this invention to provide compounds which lessen or minimize deterioration that usually accompanies the exposure of organic materials to oxidative conditions. Further objects will become apparent to those skilled in this art as the description proceeds.

The materials of the invention are prepared by reacting benzyl chloride substituted hindered phenolic compounds with β-diketones in a solvent such as alcohol and in the presence of a base, refluxing the alcohol solution to form a monoketone, reducing the monoketone to form the corresponding alcohol and converting the alcohol into an ester. The process can be carried out either batchwise or continuously as desired.

The process can be illustrated schematically by the following equations. Compounds having the general formula

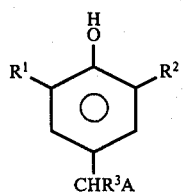
(I)

are reacted with compounds having the general formula

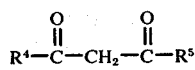
(II)

in the presence of a base acting as a catalyst while dissolved in ethanol solvent at a temperature of from about 0° C to about 120° C, forming a monoalkylated diketone having the structural formula

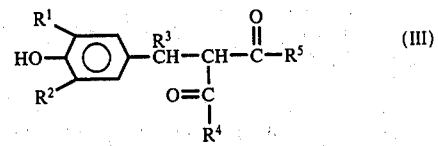
(III)

This product is refluxed in the ethanol solvent for form about 5 to about 10 hours to produce a monoketone having the structural formula

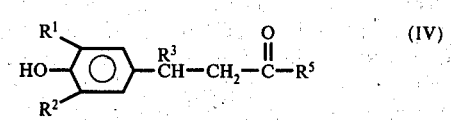
(IV)

and an ester by-product

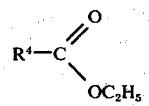

which is found in part from the solvent.

The reaction product IV is reduced to form an alcohol of the formula

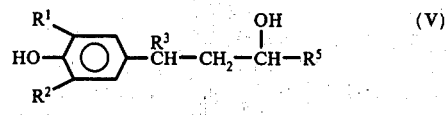
(V)

which is then reacted under ester interchange conditions in the presence of a catalyst with an ester having the general structural formula

(VI)

to yield an ester having the structural formula

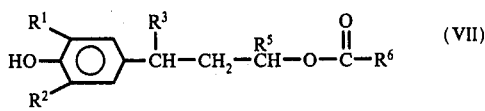 (VII)

In the structural formulas above, R¹ and R² are the same or different radicals selected from the group consisting of tertiary alkyl radicals having from 4 to 12 carbon atoms, R³ is selected from the group consisting of hydrogen and n-alkyl radicals having from 1 to 20 carbon atoms, A is a halogen selected from the group consisting of chloro, bromo, and iodo, R⁴ and R⁵ are the same or different radicals selected from the group consisting of alkyl radicals having from 1 to 10 carbon atoms, aralkyl radicals having from 7 to 15 carbon atoms, alkylene radicals having from 2 to 10 carbon atoms and aryl radicals having from 6 to 12 carbon atoms, R⁶ is selected from the group consisting of hydrogen, alkyl radicals having from 1 to 17 carbon atoms, aralkyl radicals having from 7 to 12 carbon atoms, and aryl radicals having the general formula

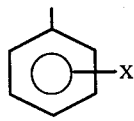

wherein X is selected from the group consisting of amino, nitro, chloro, iodo, alkoxy and alkyl radicals having from 1 to 17 carbon atoms and wherein R⁷ is an alkyl radical having from 1 to 10 carbon atoms.

Representative examples of radicals described above are tertiary alkyl radicals such as tertiary butyl, tertiary octyl and tertiary decyl, n-alkyl radicals such as methyl, ethyl, propyl, butyl, nonyl, decyl tetradecyl, hexadecyl, nonedecyl, alkylene radicals such as 1-propenyl and 2-butenyl, aralkyl radicals such as methyl phenyl and pentyl phenyl and aryl radicals such as phenyl and naphthyl.

Representative examples of the group (I) compounds are
3,5-di-t-butyl-4-hydroxy benzyl chloride,
3,5-di-t-butyl-4-hydroxy benzyl bromide,
α-methyl-3,5-di-t-butyl-4-hydroxy benzyl chloride,
α-isopropyl-3,5-di-t-butyl-4-hydroxy benzyl chloride,
α-ethyl-3,5-di-t-butyl-4-hydroxy benzyl bromide and
3,5-di-t-hexyl-4-hydroxy benzyl chloride.

Representative examples of group (II) diketones are
2,4-pentadione
1,3-diphenyl-1,3-propanedione,
1,3-dibenzyl-1,3-propanedione,
3,5-heptanedione,
8,10-heptadecadione, and
1,3-dicyclohexyl-1,3-propanedione.

Diketones where R⁴ and R⁵ are the same are the preferred ketones since cleavage may occur at either ketonic group and yield only one product.

Representative examples of group (V) alcohols produced by the reduction of group (IV) monoketones are
1-(3,5-di-t-butyl-4-hydroxyphenyl)-3-hydroxy butane,
1-(3,5-di-t-butyl-4-hydroxyphenyl)-3-hydroxy-3-phenyl propane,
1-(3,5-di-t-butyl-4-hydroxyphenyl)-3-hydroxy-4-phenyl butane,
1-(3,5-di-t-butyl-4-hydroxyphenyl)-3-hydroxy pentane,
1-(3,5-di-t-butyl-4-hydroxyphenyl)-3-hydroxy decane, and
1-(3,5-di-t-butyl-4-hydroxyphenyl)-3-hydroxy-3-cyclohexyl propane.

Representative examples of group (VI) compounds capable of forming esters are methyl methacrylate, methyl benzoate, methyl acrylate, methyl isobutyrate, ethyl acetate and methyl acetate. Representative ester interchange catalysts are materials selected from the group consisting of titanium esters and alcohol esters as described in U.S. Pat. No. 2,822,348. Preferred catalysts are pH neutral because of the sensitivity of the R¹ and R² groups to acid conditions and heat. Catalysts such as tetraisopropyltitanate, tetrabutyltitanate and polyisopropyltitanate can be used.

Representative examples of group (VI) esters are
methyl, p-aminobenzoate
methyl, p-nitrobenzoate
methyl, p-chlorobenzoate
methyl, p-methoxybenzoate and
methyl, p-methylbenzoate.

Representative examples of group (VII) compounds, esters functioning as antioxidants, are
4(3,5-di-t-butyl-4-hydroxy phenyl)-2-butyl acetate,
4(3,5-di-t-butyl-4-hydroxy phenyl)-2-butyl methacrylate,
4(3,5-di-t-butyl-4-hydroxy phenyl)-2-butyl benzoate,
4(3,5-di-t-butyl-4-hydroxy phenyl)-2-butyl propionate
4(3,5-di-t-butyl-4-hydroxy phenyl)-2-butyl butyrate.
4(3,5-di-t-butyl-4-hydroxy phenyl)-2-butyl p-aminobenzoate and
4(3,5-di-t-butyl-4-hydroxy phenyl)-2-butyl p-chlorobenzoate.

The base catalyst is most effective when a strong base is used. Representative examples of such catalysts are sodium carbonate, potassium carbonate, sodium hydroxide, potassium hydroxide, sodium alkoxide, potassium alkoxide and benzyl trimethyl ammonium hydroxide.

Esters prepared by the processes of this invention have antioxidant properties, and are capable of stabilizing polymers normally subject to oxidative degradation by incorporation into the polymers by conventional techniques such as by addition to polymer latices or by addition to the solid polymer on a mill or in a Banbury. Various polymers subjected to deterioration by oxidation can be conveniently protected by the antioxidants described herein including substituted and unsubstituted, saturated and unsaturated, natural and synthetic polymers. Oxidizable natural polymers include natural rubber in its various forms such as pale crepe and smoked sheet, balata and gutta percha. Oxidizable synthetic polymers are polymers such as those prepared from a single monomer, known as a homopolymer, or those prepared from a mixture of two or more copolymerizable monomers, known as copolymers. The monomers so copolymerized may be substituted or unsubstituted and may possess one or more double bonds, for example, diene monomers both conjugated and unconjugated and monoolefins including cyclic and acyclic monoolefins, especially vinyl and vinylidene polymers. Representative examples of conjugated dienes are 1,3-butadiene, chloroprene, isoprene, 2-methyl-1,3-butadiene, 2,3-dimetnyl-1,3-butadiene and piperylene. Representative examples of nonconjugated dienes are 1,4-pentadiene, 1,5-hexadiene, 1,4-hexadiene, dicyclopentadiene, 1,5-cyclooctadiene and ethylene norbornene. Representative examples of acyclic monoolefins are ethylene, propylene, 1-buteneisobutylene, 1-pentene and 1-hexene. Representative examples of cyclic monoolefins are cyclohexene, cycloheptene, cyclopentene, cyclooctene and 4-methyl cyclooctene. Representative examples of vinyl monomers are styrene, acrylonitrile, acrylic acid, ethyl acrylate, methyl vinyl ether, vinyl acetate and vinyl pyridine. Representative examples of vinylidene monomers are α-methyl styrene, methylmethacrylic acid, methylmethacrylate, ethyl methacrylate, glycidyl methacrylate and vinylidene chloride. Representative examples of synthetic polymers which can be protected by the antioxidants of this invention are polychloroprene, homopolymers of conjugated 1,3-dienes such as polyisoprenes and polybutadienes having essentially all of their repeat units combined in a cis-1,4 structure; copolymers of conjugated 1,3-dienes such as isoprene and butadiene with up to 50 percent by weight of at least one copolymerizable monomer including ethylenically unsaturated monomers such as styrene or acrylonitrile; butyl rubber which is a polymerization product of a major proportion of a monoolefin and a minor proportion of a multiolefin such as butadiene or isoprene; polyurethanes containing carbon to carbon double bonds and polymer and copolymers of monoolefins containing little or no unsaturation such as polypropylene, ethylene propylene copolymers, polyethylene and terpolymers of ethylene, propylene and a nonconjugated diene such as dicyclopentadiene, 1,4-hexadiene, ethylene norbornene and methylene norbornene.

The amount of antioxidant used to stabilize polymers can vary widely. Generally from 0.01 to 10 percent by weight based on the weight of the polymer will be used. In unsaturated polymers the amount used will generally range from 0.10 to 5.0 percent by weight based on the weight of the polymer. A more preferred range would be from 0.5 to 2.0 percent by weight based on the weight of the polymer. Mixtures of anti-oxidants can be used if desired.

When an ester of this invention is derived from an unsaturated compound such as butyl acrylate, the antioxidant contains ethylenic unsaturation and can be copolymerized into the polymer chain forming a self-stabilized polymer. In such polymers, the antioxidant is not extractable by common solvents or by washing.

When the esters are derived from saturated compounds, copolymerization is not possible. In this case, the ester is added to the polymer using conventional methods well known to those skilled in this art, such as by addition to the solid polymer on a mill or in a Banbury.

The polymer usually will contain other compounding materials such as additives and reinforcing materials used with vulcanized rubber products. Representative examples of such additives are metal oxides, reinforcing agents, pigments, fillers, softening agents, other antioxidants, plasticizing agents, curing agents and the like.

The following examples illustrate the practice of the present invention. Unless otherwise indicated, all parts and percentages are by weight.

EXAMPLE I

A 2-liter flask was charged with 105 grams (1.05 moles) of acetyl acetone, 142 grams (1.025 moles) of $K_2CO_3$ and 1 liter of ethanol. The mixture was agitated. To this mixture 245 grams (1.0 mole) of 3,5-di-t-butyl-4-hydroxy benzyl chloride was added dropwise over a 1 hour period. The mixture became thick as the intermediate monoalkylated diketone was formed. The mixture was heated to a vigorous reflux with stirring for six hours, then cooled to room temperature. Fifteen grams (0.4 mole) of sodium borohydride was slowly added portionwise over a period of 15 minutes. The mixture was then stirred at 40° C for 4 hours and allowed to stand overnight at room temperature. After standing, the salt was hydrolyzed by adding a 1:1 mixture of concentrated hydrochloric acid and water. Hydrolysis was considered complete when gas evolution ceased. Potassium chloride that formed as a by-product was filtered off. Ethanol was removed and the residue was poured into cold water and allowed to stand for one to two hours until crystallization of the product was complete. The product was filtered and allowed to air dry yielding 97 percent (269 grams) of 4-(3,5-di-t-butyl-4hydroxy phenyl)butan-2-ol having a melting point between 62° and 67° C.

EXAMPLE II

A 2-liter flask was charged with 97.9 grams of 4-(3,5-di-t-butyl-4-hydroxyphenyl) butane-2-one dissolved in 150 milliliters of tetrahydrofuran. Seven grams of lithium aluminum hydride reducing agent suspended in 300 milliliters of tetrahydrofuran was added to the solution formed over a 30 minute period during which time the temperature rose to 50° C. After stirring for two hours, a solution of a mixture of 150 milliliters of water and 15 milliliters of concentrated hydrochloric acid was carefully added to decompose the excess reducing agent. The resulting mixture was filtered and the filtrate allowed to evaporate to dryness, leaving a residue containing the product. The residue crystallized upon the addition of a small amount of hexane. 95.9 Grams of 4-(3,5-di-t-butyl-4-hydroxyphenyl) butane-2-ol was recovered with a melting point between 66° and 68° C.

EXAMPLE III

A 1 liter flask was charged with a mixture of 69.5 grams (0.25 mole) of 4-(3,5-di-t-butyl-4-hydroxyphenyl) butane-2-ol, 350 milliliters of methyl methacrylate, 0.5 gram of hydroquinone and 5 grams of tetraisopropyl titanate as the catalyst. The mixture was heated to reflux and a methanolmethylmethacrylate azeotrope slowly distilled off over a 3.5 hour period. The reaction flask was cooled slightly and 25 milliliters of water was added dropwise to hydrolyze the catalyst. The reaction mixture was allowed to cool to room temperature. The mixture was stirred 15 minutes longer and then filtered through diatomaceous earth. One hundred milliliters of hexane was added to the filtrate which separated into organic and inorganic phases. The organic phase containing the product in hexane was separated and dried over magnesium sulfate. The hexane was evaporated to obtain 82 grams (95 percent) of 4-(3,5-di-t-butyl-4-hydroxyphenyl)-2-butyl methacrylate. The boiling point of this compound was 150° to 155° C at 0.15 milliliters of mercury pressure.

EXAMPLE IV 4-(3,5-di-t-butyl-4-hydroxyphenyl) butane-2-ol was prepared by catalytic hydrogenation of 84.8 grams of 4-(3,5-di-t-butyl-4-hydroxyphenyl) butane-2-one in 400 milliliters of ethanol solvent in the presence of 10 grams of copper chromite catalyst at 150° C, and 1000 pounds per square inch pressure in a one-liter autoclave. Reduction was complete in three hours. The catalyst was filtered off and the filtrate was evaporated. The residue was crystallized by the addition of hexane to yield 82.9 grams of a white solid product (97 percent yield) having a melting point between 64° and 66° C.

The examples given illustrate the invention. Example I illustrates alkylation of the starting compound; Example II a reduction without isolation of the product of the alkylation reaction; Example III the preparation of a transesterification of the product prepared in Example II and Example IV is a reduction of the product of Example I, and may be transesterified as shown in Example II.

Some of the intermediate compounds produced using the process of this invention also have anitoxidant properties. The 4-(3,5-di-t-butyl-4-hydroxyphenyl) butane-2-ol made in Examples I and II was tested for antioxidant activity by measuring the oxygen absorption at 100° C of a film of a styrene/butadiene copolymer which contained one part of antioxidant per 100 parts of styrene/butadiene rubber hydrocarbon. The antioxidant was added on a mill in free form and not copolymerized with the polymer. The result is shown in Table 1 below.

TABLE 1

| Antioxidant | Hours to Absorb 1 % Oxygen |
|---|---|
| 4-(3,5-di-t-butyl-4-hydroxyphenyl)-butane-2-ol | 452 |
| butylated octylated phenol (control) | 342 |

The processes of this invention, when run continuously, can be illustrated by the equations shown below, $R^1$, $R^2$, $R^3$, $R^4$, $R^5$, $R^6$ and $R^7$ being the same radicals as described and exemplified above.

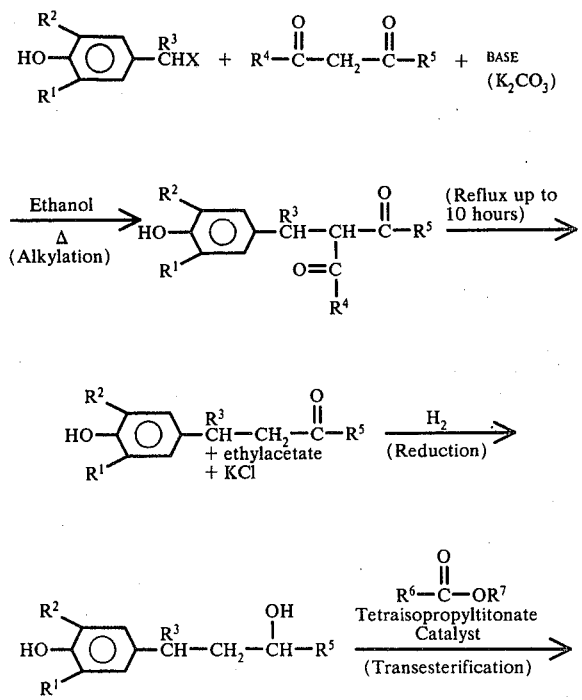

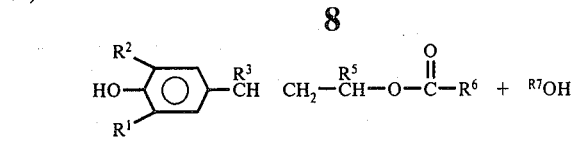

As indicated in Table 1, the process can be operated continuously. When operated in this manner, step 1 of the process proceeds as in a normal alkylation. After the formation of the monoketone, the salt formed is filtered off, a reduction catalyst is added, the ketone is reduced to an alcohol, the ethanol solvent is removed and replaced with the ester-forming compound and the transesterification catalyst for the reaction to the final product.

The transesterification product of Example III was copolymerized using emulsion polymerization techniques with monomer systems containing 75 parts of butadiene, 25 parts of styrene; and 67 parts of butadiene, 33 parts of acrylonitrile, both containing 1.50 parts of the antioxidant being tested. The antioxidant control was a butylated reaction product of p-cresol and dicyclopentadiene, sold by The Goodyear Tire & Rubber Company as Wing-Stay L. Before oxygen absorption tests were run on the polymers, the polymers were extracted for 48 hours with methanol to remove any unreacted free monomeric antioxidants that may be present, dried again, and then dissolved in benzene. The benzene solutions were poured into aluminum trays and the solvent was allowed to evaporate. The resulting films were placed in an oxygen absorption apparatus. The amount of oxygen absorbed in a particular interval of time was determined and is listed in the following Table 2. The testing procedure is described in further detail in *Industrial and Engineering Chemistry*, vol 43, page 456 (1951) and *Industrial and Engineering Chemistry*, Vol 45, page 392 (1953).

TABLE 2

|   | Antioxidant | PHR | Copolymer | Hours to Absorb 1 % Oxygen |
|---|---|---|---|---|
| A | (control) | 1.5 | SBR | 15 |
| B | Ex. III | 1.5 | SBR | 536 |
| C | Ex. III | 1.5 | NBR | 315 |
| D | Ex. III | 1.5 | NBR | 264 |

While certain representative embodiments and details have been shown for the purpose of illustrating the invention, it will be apparent to those skilled in this art that various changes and modifications may be made herein without departing from the spirit or the scope of this invention.

What is claimed is:

1. A process comprising reacting compounds having the general structural formula

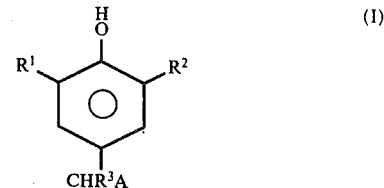

(1)

with compounds having the general structural formula

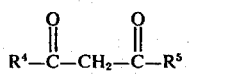 (II)

in the presence of a basic catalyst while dissolved in ethanol solvent to yield a monoalkylated diketone having the structural formula

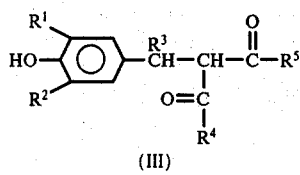 (III)

which is refluxed in solution to produce an alkylated ketone having the structural formula

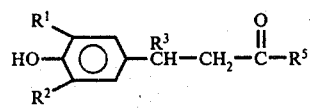 (IV)

and which may reduce without isolation or purification to form an alcohol having the general structural formula

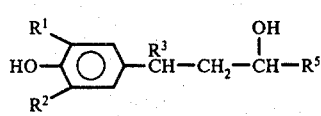 (V)

wherein the ethanol solvent is removed and replaced with an ester forming compound of the general formula

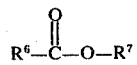 (VI)

while in the presence of a catalytic amount of an ester interchange catalyst to yield an ester with the structural formula

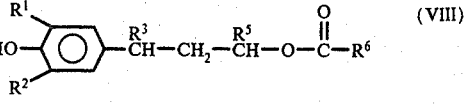 (VIII)

wherein in said formulas $R^1$ and $R^2$ are the same or different radicals selected from the group consisting of tertiary alkyl radicals having from 4 to 12 carbon atoms, $R^3$ is selected from the group consisting of hydrogen and n-alkyl radicals having from 1 to 20 carbon atoms, A is selected from the group consisting of chloro, bromo and iodo, $R^4$ and $R^5$ are the same or different radicals selected from the group consisting of alkyl radicals having from 1 to 10 carbon atoms, alkylene radicals having from 2 to 10 carbon atoms, aryl radicals having from 6 to 12 carbon atoms, $R^6$ is selected from the group consisting of hydrogen, alkyl radicals having from 1 to 17 carbon atoms, aralkyl radicals having from 7 to 12 carbon atoms, and aryl radicals having the general formula

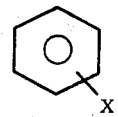 (VII)

wherein X is selected from the group consisting of amino, nitro, chloro, alkoxy and alkyl radicals having from 1 to 17 carbon atoms and wherein $R^7$ is an alkyl radical having from 1 to 10

2. A process comprising reacting compounds having the general formula

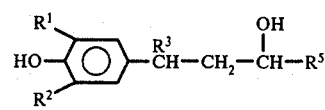

with ester forming compounds of the general formula

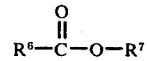

in the presence of a catalytic amount of an ester interchange catalyst to yield an ester with the structural formula

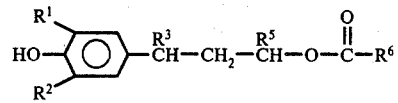

wherein in said formulas $R^1$ and $R^2$ are the same or different radicals selected from the group consisting of tertiary alkyl radicals having from 4 to 12 carbon atoms, $R^3$ is selected from the group consisting of hydrogen and n-alkyl radicals having from 1 to 20 carbon atoms and $R^5$ is selected from the group consisting of alkyl radicals having from 1 to 10 carbon atoms, alkylene radicals having from 2 to 10 carbon atoms, and aryl radicals having from 6 to 12 carbon atoms, $R^6$ and $R^7$ are selected from the group consisting of alkyl radicals having from 1 to 5 carbon atoms and alkylene radicals having from 2 to 5 carbon atoms.

3. A process as described in claim 1 wherein compounds having the general formula (I) are selected from the group consisting of
3,5-di-t-butyl-4-hydroxy benzyl chloride,
3,5-di-t-butyl-4-hydroxy benzyl bromide,
α-methyl-3,5-di-t-butyl-4-hydroxy benzyl chloride,
α-isopropyl-3,5-di-t-butyl-4-hydroxy benzyl chloride, α-ethyl-3,5-di-t-butyl-4-hydroxy benzyl bromide, and
3,5-di-t-hexyl-4-hydroxy benzyl chloride.

4. A process as described in claim 1 wherein compounds having the general formula (II) are selected from the group consisting of
2,4-pentadione,
1,3-diphenyl-1,4-propanedione,
1,3-dibenzyl-1,3-propanedione,
3,5-heptanedione,
8,10-heptadecanedione, and
dicyclohexyl-1,3-propanedione.

5. A process as described in claim 4 wherein compounds having the general formula (VI) are selected from the group consisting of
methyl methacrylate,
methyl acrylate,
methyl benzoate,
methyl isobutyrate, and
ethyl acetate.

6. A process as described in claim 5 wherein the transesterification catalyst is selected from the group consisting of
tetraisopropyl titanate,
tetrabutyl titanate and
polyisopropyl titanate.

7. A process as described in claim 1 where 4-(3,5-di-t-butyl-4-hydroxyphenyl)-butane-2-one is reacted with lithium aluminum hydride to yield 4-(3,5-di-t-butyl-4-hydroxyphenyl)-butane-2-ol.

8. A process as described in claim 2 where 4-(3,5-di-t-butyl-4-hydroxyphenyl)-butane-2-ol is esterified by reaction with methylmethacrylate in the presence of tetraisopropyl titanate to yield 4-(3,5-di-t-butyl-4-hydroxyphenyl)-2-butyl methacrylate.

* * * * *

UNITED STATES PATENT OFFICE
CERTIFICATE OF CORRECTION

PATENT NO. : 3,989,741
DATED : November 2, 1976
INVENTOR(S) : Dane K. Parker

It is certified that error appears in the above-identified patent and that said Letters Patent are hereby corrected as shown below:

Column 10, line 61, delete "alkylene" and substitute --alkenyl--.

Column 11, line 12, delete "4" and insert --2--.

Column 11, line 17, delete "methyl benzoate".

Signed and Sealed this

Twenty-second Day of May 1979

[SEAL]

Attest:

RUTH C. MASON
Attesting Officer

DONALD W. BANNER
Commissioner of Patents and Trademarks